US009204987B1

(12) United States Patent
Breibart

(10) Patent No.: US 9,204,987 B1
(45) Date of Patent: Dec. 8, 2015

(54) DEVICE FOR ENHANCING AWARENESS OF HEAD POSITIONING

(76) Inventor: Joan Breibart, New York, NY (US)

(*) Notice: Subject to any disclaimer, the term of this patent is extended or adjusted under 35 U.S.C. 154(b) by 1417 days.

(21) Appl. No.: 12/799,052

(22) Filed: Apr. 16, 2010

(51) Int. Cl.
*A61F 5/00* (2006.01)
*A61F 5/055* (2006.01)

(52) U.S. Cl.
CPC ..................... *A61F 5/055* (2013.01)

(58) Field of Classification Search
CPC ......... A45D 40/30; A45D 44/00; A45D 8/12; A45D 44/002; A45D 44/22; A45D 8/36; A61M 16/0683; A61M 16/0666; A61M 16/06; A61M 16/0833; A61M 16/085; A61M 2230/432; A61M 16/0488; A61M 16/0493
USPC ................ 602/5, 17–19, 32, 36, 39; 128/848, 128/857–862, DIG. 23; 606/241–245; 441/108, 110, 112–115, 117, 119; 482/55, 121–126, 10; 272/93–95, 126, 272/135, 136, 139; 273/DIG. 17–DIG. 19; 2/2
See application file for complete search history.

(56) References Cited

U.S. PATENT DOCUMENTS

| | | | | |
|---|---|---|---|---|
| 1,618,273 A * | 2/1927 | Davidson | ..................... | 482/124 |
| 2,097,376 A * | 10/1937 | Marshman | ..................... | 482/124 |
| 4,540,173 A * | 9/1985 | Hopkins, Jr. | ................. | 482/124 |
| 4,832,333 A * | 5/1989 | Lockett | ........................ | 482/10 |
| 5,308,305 A * | 5/1994 | Romney | ....................... | 482/124 |
| 5,372,565 A | 12/1994 | Burdenko | | |
| 5,752,900 A | 5/1998 | Holland, Jr. | | |
| 5,895,363 A * | 4/1999 | Preijde | ........................ | 600/595 |
| 6,322,482 B1 | 11/2001 | Kim | | |
| 8,613,690 B1 * | 12/2013 | Thompson | ..................... | 482/10 |
| 2003/0195092 A1 * | 10/2003 | Basting | ........................ | 482/124 |
| 2004/0152569 A1 | 8/2004 | Lerner | | |
| 2005/0043154 A1 * | 2/2005 | Atrizadeh | ..................... | 482/124 |
| 2007/0094768 A1 * | 5/2007 | Moudgill | ......................... | 2/171 |
| 2009/0062087 A1 * | 3/2009 | Poppinga | ..................... | 482/124 |
| 2013/0053225 A1 * | 2/2013 | Meyer | ........................... | 482/124 |

* cited by examiner

*Primary Examiner* — Michael Brown
(74) *Attorney, Agent, or Firm* — R. Neil Sudol; Henry D. Coleman

(57) ABSTRACT

A device and an associated method for assisting in maintaining awareness of skeleton-muscular alignment includes a chest harness attachable to a user about the thorax and a head harness. Elongate tensile member segments extend from opposite ends of a back strap right at the beginning of the armpit of the chest harness. These tensile member segments are connectable at their distal ends to the feet of the user. Further tensile member segments extend from opposite ends of the back strap of the harness and are connectable at their distal ends to or about the user's hands. The headband includes an elastic cord that is wound about the headband and is connectable at opposite ends to the hands or wrists of the user.

9 Claims, 5 Drawing Sheets

DEVICE FOR ENHANCING AWARENESS OF HEAD POSITIONING

BACKGROUND OF THE INVENTION

This invention relates to a device for assisting a user in finding correct head placement, which comes from freeing the neck.

A common problem with people's posture is head alignment. The typical human head weighs about 10 to 12 pounds—the same amount as a regulation bowling ball. While the head's weight is obviously held vertically erect by the neck, it is also supported by a host of other muscles in our shoulders and upper back. All of these muscles work together to help the head defy gravity and stay in proper alignment with the rest of the body.

When the head is in proper alignment over the shoulders when one is sitting, standing, or moving, the body's tissues and muscles are able to move smoothly, efficiently and painlessly. This ideal is associated with what is considered "good" posture. It sounds like a simple goal, but actually requires consistent and constant body awareness.

It is estimated that 90 percent of the population fails to some degree to maintain proper head alignment. This means that people unconsciously allow their heads to jut forward over the center of their shoulders. This is typically described as forward head syndrome. Usually, due to posture associated with eating, computer work, video games, texting, etc., one is likely to let the cervical spine slump into flexion. In time the injured muscles become weak and the joints of the lower cervical spine lose extension mobility. At the same time, the upper cervical spine is held in extension in order to keep the head and eyes level. Chronic forward head postures causes a strain on the ligaments and muscles in the posterior lower cervical and upper thoracic spine. This syndrome is characterized by generalized, non-specific pain in the neck and upper back, headaches and occasional referred pain into the upper extremities. The upper trapezius, elevator scapulae and rhomboid major muscles are most often involved. In addition to the pain associated with forward head, if untreated and uncorrected, this posture can lead to rounded shoulders and a premature "dowagers hump."

While the result of forward posture is most visible around the neck and shoulders, it affects the body's entire muscular structure and its internal systems. When the head juts forward, the body's center of gravity shifts. To compensate for this shift, the upper body pulls backward. To compensate for the upper body's shift, the hips tilt forward. For every inch the head moves forward, that "bowling ball" gains 10 pounds as far as the muscles in the neck and back are concerned as they have to work harder to keep the head—led by the chin—from dropping forward onto the chest. Lung capacity is reduced. The gastrointestinal system, particularly the large intestine, is affected. The forward head creates shortened, contracted muscles in front and a weakened back. Contracted jaw muscles cause TMJ problems. As forward head posture is progressive and chronic, most sufferers are unaware of what is causing their discomfort and often write off the pain across their shoulders as "stress."

OBJECTS OF THE INVENTION

An object of the present invention is to provide physical feedback which will help one improve one's posture over time.

Another object of the present invention is to provide such a device that heightens awareness of an individual of his or her skeleto-muscular alignment or misalignment. It is believed that such a heightened awareness will carry over into normal daily activities and eventually enhance ease and comfort in standing and seated activities.

These and other objects of the present invention will be apparent to one skilled in the art from the drawings and descriptions herein.

Although every feature of the invention is attained in at least one embodiment of the invention, there is not necessarily any one embodiment that achieves all of the objects of the invention.

SUMMARY OF THE INVENTION

The present invention is directed to increasing a person's awareness of the position and inclination of his or her head. The device in accordance with the present invention helps the user feel the correct position of the head.

A device for increasing awareness of head positioning comprises, in accordance with the present invention, a chest harness attachable to a user about the thorax and a head harness. Elastic elongate tensile members linked to the chest harness are attachable at least indirectly to the hands and feet of a user, for example, about the user's hands, or to the fingers. The chest harness and the tensile members serve in part to stabilize the scapular regions, to elevate the breastbone and to connect the limbs. The head harness includes one elastic tensile member that wraps the head and that is preferably connectable to the thumbs of the user. The chest harness, head harness and associated tensile members (e.g., bungee cords) assist a user in finding an awareness of proper skeletonmuscular alignment of the head/neck area. In other words, an assembly for assisting a user in finding proper head/neck positioning and heightening an awareness of skeleton-muscular alignment of the head and neck comprises, in accordance with the present invention, (a) a chest harness attachable to a user about the thorax, (b) elongate and elastic tensile members attached to the harness and attachable at ends to a user at least indirectly to the user's hands and feet, (c) a head harness attachable to the user's head, and (d) at least one tensile member that extends from the headband to the user's hands. Preferably the tensile member of the head harness is a single elastic tensile member such as a bungee cord that wraps the head and comes out of the band and crosses so that the two ends of the cord are attachable to the user's thumbs.

In accordance with a major feature of the present invention, the head-harness tensile member is wound about the head harness so that pulling on opposite ends of the second tensile member exerts a compressive force on the user's head. This tensile member may extend through an annular channel formed by loops or strips of fabric attached to the head harness, which does take the form of a headband.

The chest-harness tensile members are preferably two in number. During use of the assembly, one of the chest-harness tensile members is attached at opposite ends to the hands while the other chest-harness tensile member is attached to the feet. The chest harness includes a back strap configured to extend horizontally across the user's back, and the first two tensile members are slidably connected to the back strap so as to extend parallel thereto. More specifically, the chest harness may include elements such as loops or elongate strips of fabric that are connected to the back strap so as to define two parallel paths for passage of the first tensile members. If loops were used to define the paths for the tensile members, the loops would be spaced from one another in the manner of belt loops on trousers. Preferably, elongate strips of fabric define the paths of the chest-harness tensile members, the fabric strips being stitched to the back strap to form two elongate lumens or channels. The lumens or channels each have two outlet openings located at opposite sides of the back strap.

The chest harness may particularly include a circumferential main strap for substantially horizontally encircling the user's thorax and a pair of shoulder straps each connected at one end to a back portion of the main strap and at an opposite end to a front portion of the main strap. The chest harness may further include a buckle attached to the main strap and length adjustment members attached to the main strap and the shoulder straps.

The chest harness is locatable at the breastbone in front and on the shoulder blades in back of the user. The chest harness has a front strap continuous with the back strap and is configured to locate the front strap above breasts of a female user.

A head and neck position awareness enhancement method in accordance with the present invention comprises (i) providing a head harness and a chest harness, the chest harness having a plurality of at least partially elastic first tensile members, the head harness having at least one at least partially elastic second tensile member. The method further comprises (ii) attaching the chest harness about a user's thorax, (iii) attaching the head harness to the user's head, (iv) attaching ends of the first tensile members to the user's hands and feet, (v) attaching ends of the second tensile member to the user's hands, and (vi) holding the hands and feet in prescribed positions while the first tensile members are attached to the hands and feet and the second tensile members are attached to the hands.

It is contemplated that the tensile members are coupled to the hands and feet of the user via non-elastic bands at the free ends of the tensile members. Other alternative forms of attachment might be suitable in limited applications, for example, gloves and socks or booties, rings, straps, looped-back end portions of the tensile members, etc.

It is to be noted that the chest harness of the head/neck awareness tool of the present invention may be used without the head harness.

A head and neck positioning awareness device, particularly including a head harness and associate tensile member, in accordance with the present invention creates a head adjustment without having the user lying prone and having a doctor or therapist work on the user's body. The user sees and feels alignment while using the device and looking in a mirror. It is to be noted that no one can fix a forward head permanently by a manual (chiropractic or other) adjustment. Within hours, the body's memory and muscles return the head back to the forward inclination. It is only by feeling the correct placement that one can, on a multiple daily basis, for instance, feel proper placement and consequently make the adjustment mentally until it starts to happen physically. The alignment positions and mental exercises help to strengthen the back extensors, etc., but most of the change is through awareness training.

Preferably, the user uses the head position awareness tool of the present invention on a daily basis. During normal daily activities, the user brings his or her awareness to bear on head position, to become aware of when the head is slumping and jutting forward.

DETAILED DESCRIPTION

Figure 1:
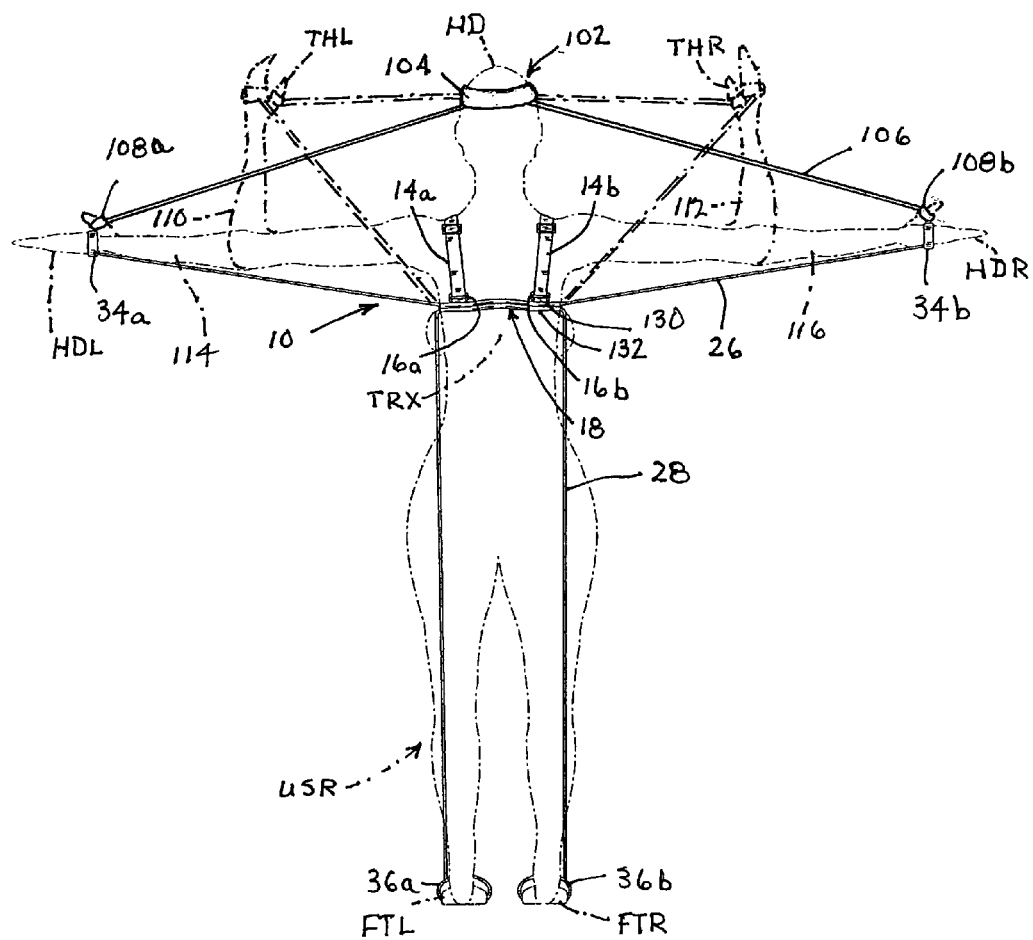
FIG. 1 is a rear elevational view of a head/neck positioning assist device in accordance with the present invention, showing the device in two use positions with an individual user depicted in phantom lines.
Figure 2:
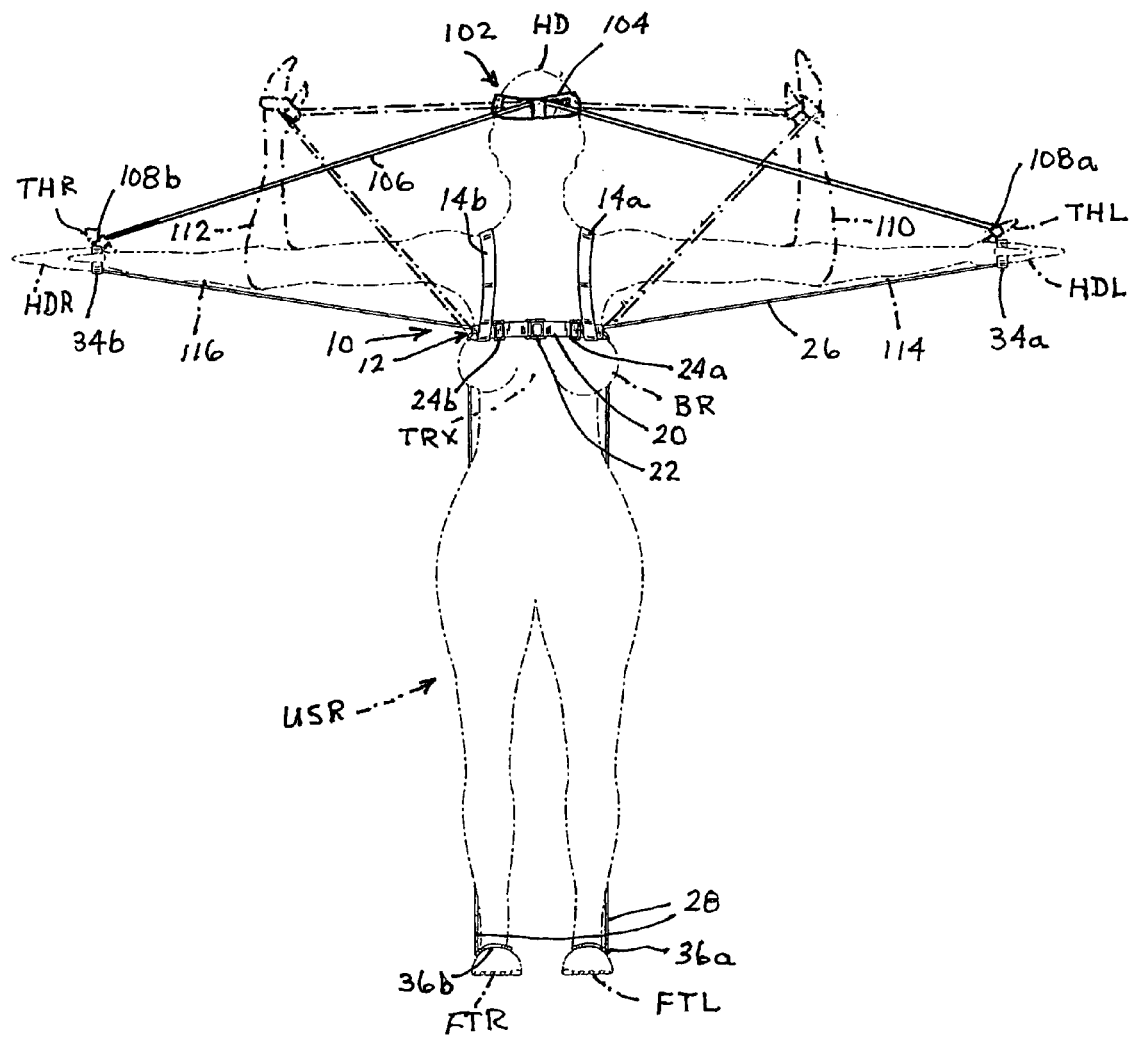
FIG. 2 is a front elevational view of the device of FIG. 1, also showing the device in two use positions with an individual user shown in phantom lines.
Figure 3:
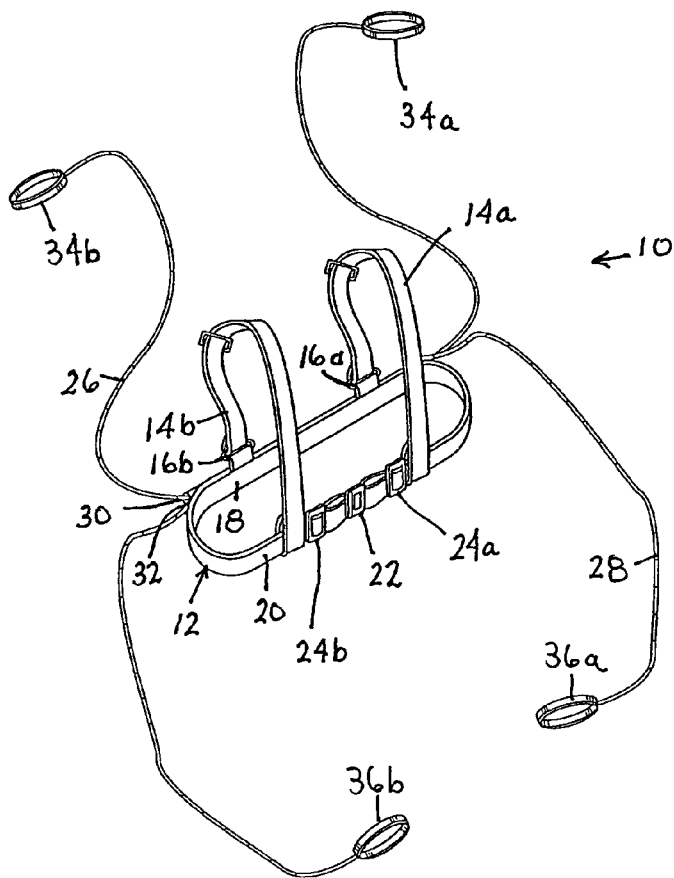
FIG. 3 is a perspective view of a chest harness device included in the device of FIGS. 1 and 2.
Figure 4:
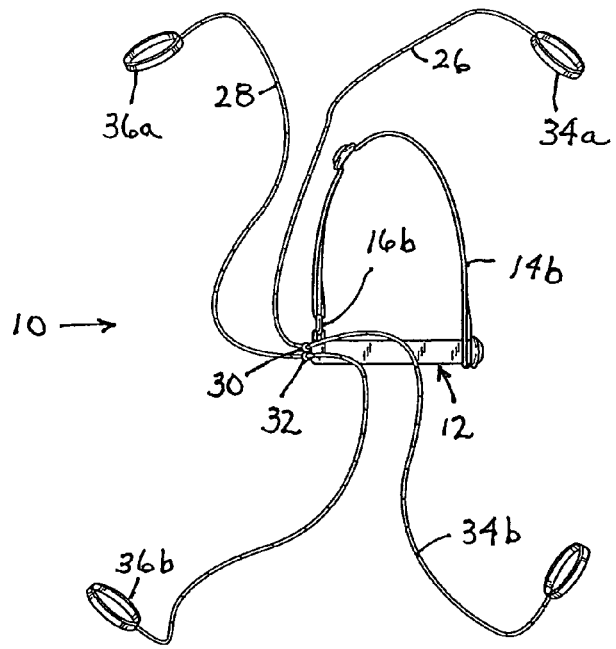
FIG. 4 is a right side elevational view of the chest harness of FIGS. 1-3, the left side being a mirror image of the right side.
Figure 5:
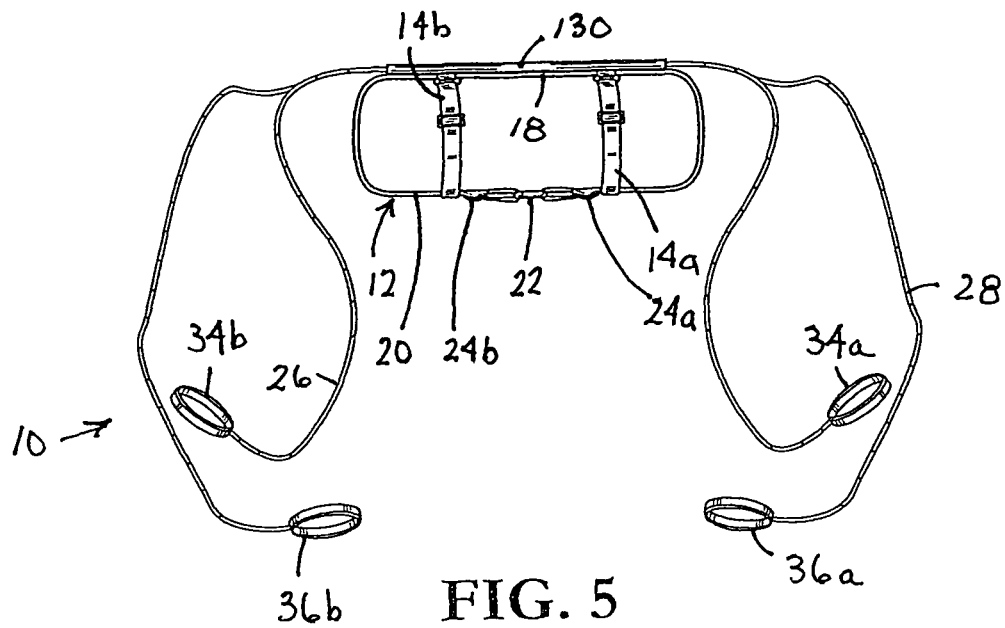
FIG. 5 is a top plan view of the chest harness of FIGS. 1-4.
Figure 6:
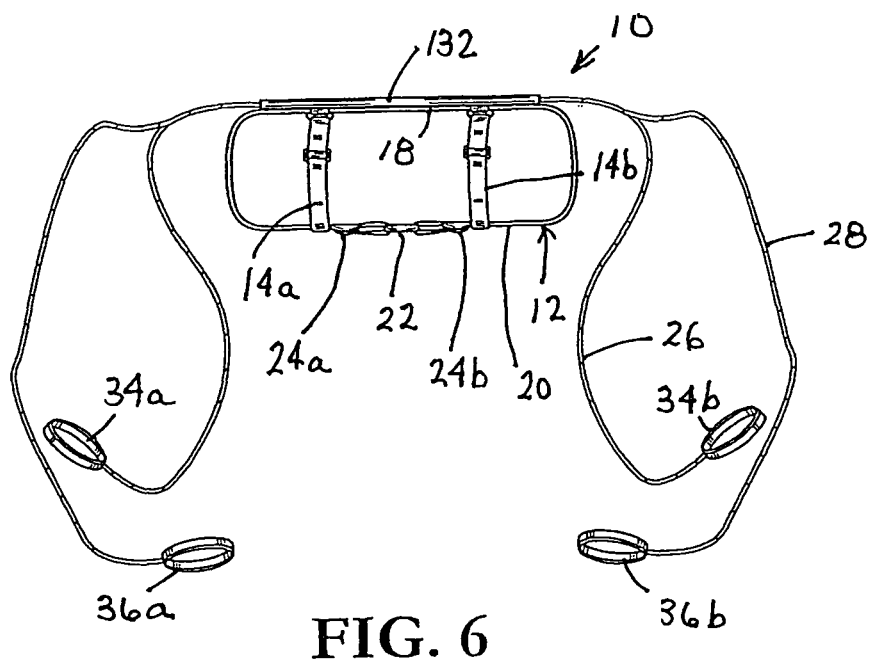
FIG. 6 is a bottom plan view of the chest harness of FIGS. 1-5.

As depicted in the FIGS. 1 and 2, a device for assisting a user USR in adopting and maintaining proper head positioning and more particularly heightens an individual's awareness of his or her head positioning comprises a chest harness 10 attachable to the user USR about the user's thorax TRX and further includes a head harness 102 attachable to the user's head HD.

As depicted in FIGS. 1-6, chest harness 10 includes a circumferentially extending main strap or belt 12 that encircles the user USR in a generally horizontal plane about the chest or thorax TRX. Chest harness 10 further includes a pair of shoulder straps 14a and 14b connected at a rear side via respective flattened or oblate rings 16a and 16b to a back strap portion 18 of main strap 12. On their front sides, shoulder straps 14a and 14b are looped about a front strap portion 20 of main strap 12. The front side of each shoulder strap 14a and 14b is sewn to itself above front strap portion 20. During use of the head/neck awareness enhancement device, front strap portion 20 of main strap or belt 12 is located on a front side of user USR at the breastbone, and just above the breasts BR (FIG. 2) where the user is a woman. Back strap 18 is located on the shoulder blades in the back. Chest harness 10 is thus located entirely above the abdominal region of the user USR.

Main strap 12 is provided in front strap portion 20 with a spring-loaded buckle 22 that is releasable upon application of finger pressure. Front strap portion 20 is further provided with a pair of length-adjustment elements 24a and 24b for symmetrically adjusting the fit of main strap 12 to the chest or thorax TRX of the user USR.

Chest harness 10 is provided with a pair of at least partially elastic first elongate tensile members 26 and 28 (e.g., bungee cords) that slidably extend through respective channels or passageways (not separately designated) along a rear surface of back strap portion 18. Stitching one or two elongate fabric strips 130 and 132 to back strap portion 18 forms the channels or passageways.

During use of the head/neck positioning awareness enhancement device, chest-harness tensile member 26 is attached at opposite ends via bands or straps 34a and 34b to the hands (or wrists) of the user USR, while chest-harness tensile member 28 is attached to the user's feet via bands or straps 36a and 36b. Back strap portion 18 is configured to extend horizontally across the user's back, as shown in FIG. 1, and tensile members 26 and 28 are slidably connected to the back strap via the channel-forming fabric strips or strip sections 30, 32. Fabric strips or strip sections 30 and 32 define two parallel paths for passage of tensile members 26 and 28. The channels or passageways each have two outlet openings 30, 32 (only one shown—FIGS. 3, 4) located at opposite sides of back strap 18. The outlet openings 30, 32 are each located generally below the user's armpits.

Chest harness 10 further includes two length-adjustment elements 34a and 34b on shoulder straps 14a and 14b for enabling the user USR to adjust the effective lengths of the shoulder straps as desired.

Figure 7:
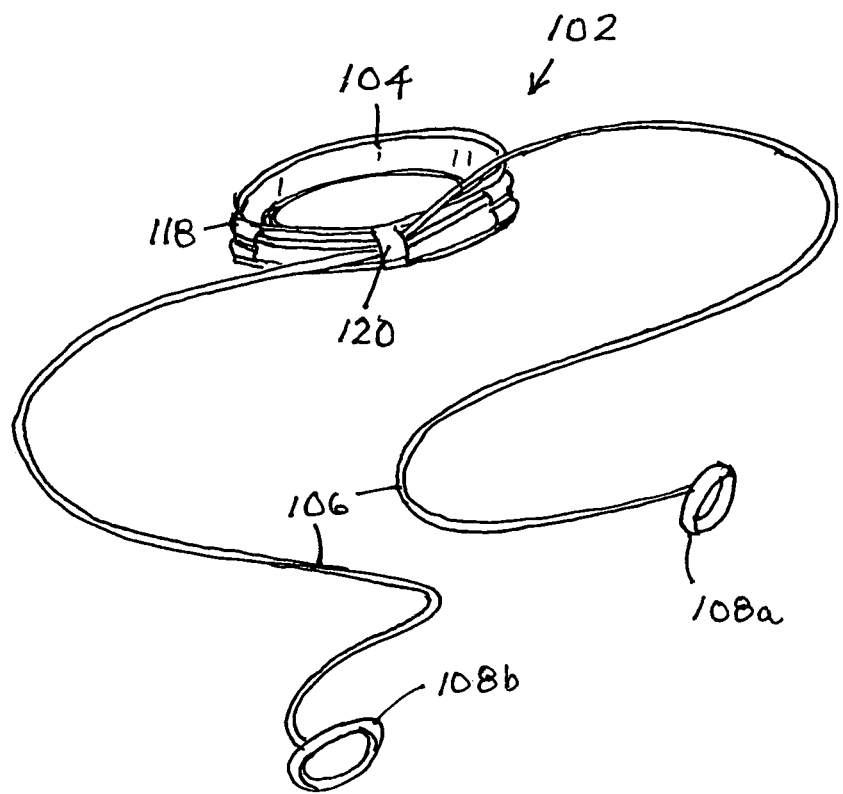
FIG. 7 is a perspective view of a head harness included in the alignment assist device of FIGS. 1 and 2.

Head harness 102 includes a headband 104 that may be partially elastic or provided with a VELCRO hook-and-loop fastener (not show) for adapting the band to the user's head size. As shown in FIG. 7, headband 104 includes an elongate and at least partially elastic second tensile member 106 that extends through a channel or passageway (not separately designated) formed on an outer surface of the headband by multiple spaced loops or an elongate fabric strip 118 sewn to the headband. Tensile member 106 is connected to and extends in part longitudinally along headband 104 in parallel relation thereto. As depicted in FIG. 7, a midsection of tensile member 106 is wound a full turn or circle about headband 104. A single loop 120 is provided at a central front position on headband 104 and forms a final guide for tensile member 106.

Tensile member 106 is linked to the head harness and attachable at ends to the user USR at least indirectly to the user's hands. Tensile member 106 (e.g., a bungee cord) is particularly provided at opposite ends with rings, bands or loops 108a and 108b for securing the tensile member to the thumbs (see FIGS. 1 and 2) of the user. Tensile member 106 is wound about headband 104 so that pulling on opposite ends of the tensile member exerts a compressive force on the user's head in the plane of the headband.

As shown in FIGS. 1 and 2, head harness 102 and chest harness 10 are used with the chest harness disposed about a user's thorax TRX, head harness 102 disposed about the user's head HD, ends of tensile members 26 and 28 coupled to the user's hands HDL, HDR and feet FTL and FTR, and ends of tensile member 106 coupled to the user's thumbs THL and THR (or hands or wrists). While the user holds his or her limbs in prescribed positions, tensile members 26, 28, and 106 apply forces to the user's torso and head that provide kinesthetic feedback to the user, increasing the user's awareness of head position and thereby assisting the user in adopting and holding proper head orientation. The user preferably enhances the awareness and feeling by looking at himself or herself in a mirror while holding one or more different positions for short times.

Chest-harness tensile member or arm bungee cord 26 crosses the user's back at the scapular region; this creates tension and when the two ends of this tensile member are pulled forward and lifted overhead, with a right angle at the elbows, as indicated in FIGS. 1 and 2 at 110 and 112 they cause the scapular region to indent and release (it is usually locked given most people's posture). Meanwhile, half segments of head-harness tensile member 106 are lengthened sideways, causing the head to "shrink" and elongate so that it can be moved backwards where it belongs. Of course, all of these posture adjustments are tiny so that when the user releases the tensile member 106 and extends the arms outwardly, as shown in FIGS. 1 and 2 at 114 and 116, the head HD will return forward. However, the user will retain a memory, if only subconscious, of correct head placement. That memory will eventually enable the user to attain a correct head position even in daily activities.

FIGS. 1 and 2 show head harness 102 with loop 120 disposed on the forehead. This position of the head harness is appropriate for the bent elbow position 110, 112. The bent elbow position 110, 112 is preferably reached by pulling bungee tensile members 106 and 26 from the front of the head.

For the arm straightened positions 114, 116, the head harness is preferably reversed, so that loop 120 is disposed on the back of the head. One best attains the arm straightened position 114, 116 by pulling the bungee tensile members 26 and 106 from the back of the head.

Tensile members 26, 28, 106 may take any form that provides sufficient tension and therefore compressive support to a user's arms and legs. Tensile members 26, 28, 106 may be elastic polymeric tubes or hoses that are commonly used in the exercise field. However, it is preferable that tensile members 26, 28, 106 take the form of bungee cords or other elongate flexible and generally completely elastic straps.

It is to be noted that chest harness 10 may be used without head harness 102.

Although the invention has been described in terms of particular embodiments and applications, one of ordinary skill in the art, in light of this teaching, can generate additional embodiments and modifications without departing from the spirit of or exceeding the scope of the claimed invention. For instance, chest harness 10 may take any form that permits the securing of flexible elastic lines or tensile members 26 and 28 to the thorax or upper torso TRX of a user. A chest or thorax harness may therefore take the form of a vest, or halter top, with appropriate reinforcement such as leather or canvas bands, to accommodate the stresses exerted by the flexible elastic members.

The arm and leg bungee chord segments (halves of tensile members 26, 28, 106) may be provided, for example, at their free ends, with length-adjustment members for accommodating limbs of different lengths.

Accordingly, it is to be understood that the drawings and descriptions herein are proffered by way of example to facilitate comprehension of the invention and should not be construed to limit the scope thereof.

What is claimed is:

1. A head harness comprising:
   a headband attachable to and disposable around a user's head; and
   a tensile member wound at least one full turn about said headband so that pulling on opposite ends of said tensile member exerts a compressive force on the user's head in a plane of the headband,
   said tensile member being provided at said opposite free ends with rings, bands or loops for securing the tensile member to the user's thumbs said tensile member having at least a segment in the form of a bungee cord.

2. The harness defined in claim 1 wherein said tensile member has end portions that extend in opposing directions from said headband.

3. The harness defined in claim 1 wherein said headband is provided with a channel or passageway, said tensile member extending through said channel or passageway.

4. The harness defined in claim 3 wherein said channel or passageway is formed by a structure taken from the group consisting of multiple spaced loops and an elongate fabric strip sewn to said headband.

5. A head harness comprising:
   a headband attachable to and disposable around a user's head; and
   a tensile member connected to and extending in part longitudinally along said headband in parallel relation thereto so that pulling in opposite directions on said tensile member exerts a compressive force on the user's head, said tensile member having at least a segment in the form of a bungee cord said tensile member being provided at opposite free ends with rings, bands or loops for securing the tensile member to the user's thumb.

6. The harness defined in claim 5 wherein said tensile member has portions that extend in opposing directions from said headband.

7. The harness defined in claim 5 wherein said tensile member is configured for attachment on opposite sides to respective ones of the user's hands.

8. The harness defined in claim 5 wherein said headband is provided with a channel or passageway, said tensile member extending through said channel or passageway.

9. The harness defined in claim 8 wherein said channel or passageway is formed in part by a structure taken from the group consisting of multiple spaced loops and an elongate fabric strip sewn to said headband.

\* \* \* \* \*